United States Patent [19]

Duparchy

[11] Patent Number: 4,533,223
[45] Date of Patent: Aug. 6, 1985

[54] PROCESS OF FORMATION OF AN IMAGE OF THE EYE FREE FROM REFLECTIONS FOR ITS RECORDING BY PICTURE TAKING AND/OR ITS OBSERVATION AND APPARATUS FOR PUTTING INTO ACTION OF THE PROCESS

[76] Inventor: Jacques Duparchy, 10 Rue Alquier Bouffard, 8100 Castres, France

[21] Appl. No.: 373,631

[22] Filed: Apr. 30, 1982

[30] Foreign Application Priority Data

May 5, 1981 [EP] European Pat. Off. ....... 81 400701.9

[51] Int. Cl.$^3$ .............................................. A61B 3/14
[52] U.S. Cl. ................................................... 351/206
[58] Field of Search ....................... 351/206, 207, 208; 354/62

[56] References Cited

U.S. PATENT DOCUMENTS 3,169,459 2/1965 Friedberg et al. ...................... 95/18
3,842,253 10/1974 Walker et al. .................... 240/41 R

FOREIGN PATENT DOCUMENTS 2410021 9/1975 Fed. Rep. of Germany .
2213046 8/1974 France .
2018413A 10/1979 United Kingdom .

Primary Examiner—Rodney B. Bovernick
Attorney, Agent, or Firm—Sandler & Greenblum

[57] ABSTRACT

A process and apparatus for forming a reflection-free image of an eye for photographing and/or observing is provided. The eye is at least partially coated with a fluorescent substance, and is illuminated with radiation of a wavelength less than or equal to the minimum wavelength of radiation emitted by the excited fluorescent substance. The reflections are then eliminated from the image by filtering out reflected radiation with wavelengths less than the minimum wavelength of radiation emitted by the excited fluorescent substance.

21 Claims, 10 Drawing Figures

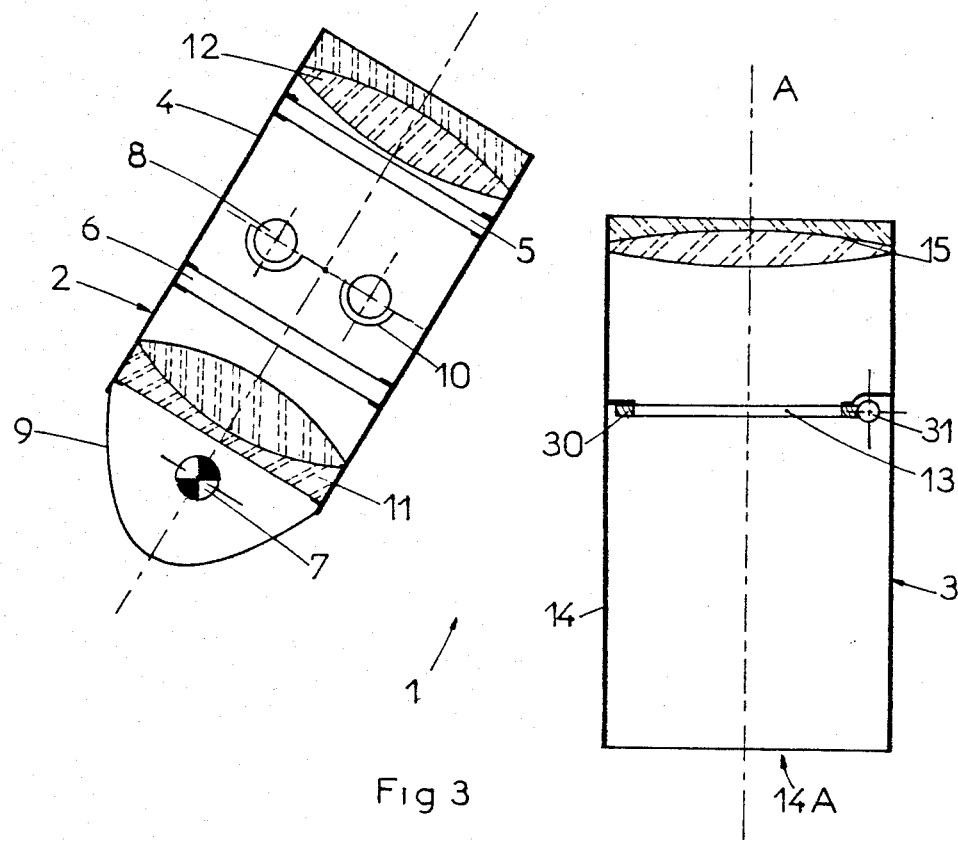
Fig 3
Fig 4
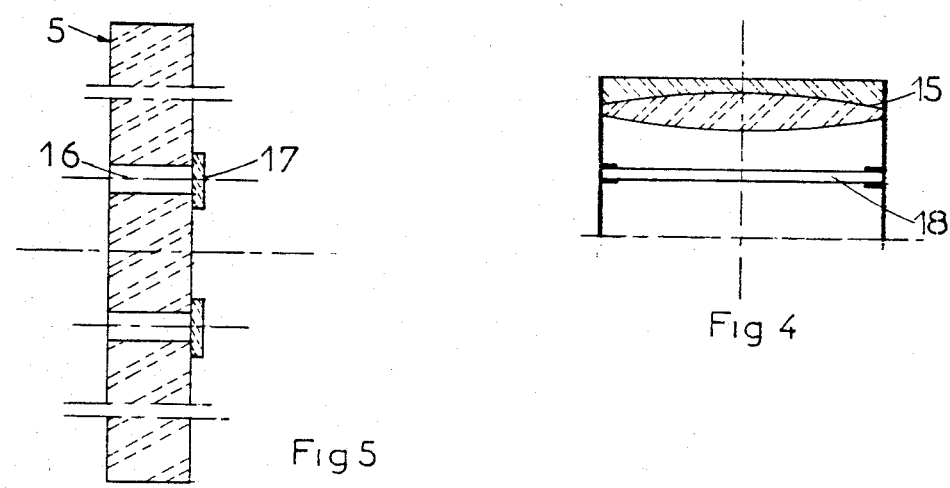
Fig 5

PROCESS OF FORMATION OF AN IMAGE OF THE EYE FREE FROM REFLECTIONS FOR ITS RECORDING BY PICTURE TAKING AND/OR ITS OBSERVATION AND APPARATUS FOR PUTTING INTO ACTION OF THE PROCESS

FIELD OF THE INVENTION

The present invention relates to observing or recording an image of the eye for the purpose of fitting ocular prostheses. The "picture taking" or recording can be performed by any processes or means providing for recordation of one or several images, and particularly by photographic methods and apparatus.

BACKGROUND OF THE INVENTION

Wearing ocular prostheses, for example, flexible or hard contact lenses, without harm to the cornea or conjunctival metabolism requires resolution of the problem of eye intolerance. To overcome the problem of intolerance, one of ordinary skill in the art at the time of fitting of the prosthesis executes various tolerance tests, including tests for the quality and quantity of tears, for controlling the centering and displacement of the prosthesis on the eye, and for observing the lacrymal film present under the prosthesis. Certain of the tests are effected with the aid of a light source emitting ultraviolet and invisible rays, particularly in the blue range, that excite a fluorescent substance dropped into the eye to emit a visible radiation. Accordingly, the circulation of the lachrymal film under the lens and zones of small lacrymal quantity can be observed.

Despite satisfactory results indicated by these tests, an ocular prostheses may ultimately be ill-tolerated by the person who wears them. Moreover, one of ordinary skill in the art can never determine with certainty the type of prosthesis best suited for a particular person. Cases may arise where sufficiently well-tolerated prostheses may be replaced by other types yielding even greater tolerance.

SUMMARY OF THE INVENTION

To overcome the above-described problems, it is advantageous to create a file of results of the different tolerance tests for various prostheses, after they have been worn with satisfactory results, according to prosthesis shape and material. By analysis of the different results, one of ordinary skill in the art will be in a position to determine with precision the type of lenses that will be best tolerated. The different tolerance results for each prosthesis may be photographically recorded. Until presently, i.e., prior to the present invention, photography and observation of an eye equipped with a lens posed major problems. Heretofore, to take a photograph or make a visual observation, one of ordinary skill in the art typically used a light source formed by a lamp and/or a flash lamp, wherein one portion of the emitted radiation would reflect off the surface being photographed and/or observed, resulting in masking of certain critical zones required to be seen for correct interpretation of the result.

An object of the present invention is to overcome the above-described problems by means of a process for removing the reflections from the light source, particularly at the instant of photography and/or observation of a fluoroscopic image of the eye. To this end, a process is provided for forming an image of the eye, for photographing and/or observing, where the image so-formed is free from reflections off the eye and/or its prosthesis which otherwise would arise fromm a light source which emits ultra-voilet and visible rays to excite a fluorescent substance dropped into the eye, the excitation manifesting itself by emission of visible rays having wavelengths greater than or equal to a value $\lambda 1$. This process is characterized in part in that the wavelengths of all or a major portion of the rays emitted by the light source are less than or equal to $\lambda 1$, and the rays issuing from the eye are filtered to select only rays appropriate for the fluorescent substance, thus removing at the level of the image to be photographed and/or observed the reflections of light from the light source off the eye and/or the prosthesis.

Another object of the present invention is to provide an apparatus for the practice of the above-described process, the apparatus including at least one luminous light source; at least one optical apparatus for the formation of the image; and at least one recording apparatus and/or at least one observation apparatus, and further including a filter for selecting or passing rays of a wavelength less than $\lambda 1$ which are emitted by a lamp and/or a flash lamp associated with a light source, and a filter associated with the optical apparatus for selecting rays emitted by the fluorescent substance.

BRIEF DESCRIPTION OF THE DRAWINGS

FIG. 3 is a schematic top view of an apparatus according to the present invention;

FIG. 4 illustrates a second embodiment of the present invention;

FIG. 5 illustrates further details of the embodiment shown in FIG. 4;

DETAILED DESCRIPTION

Figure 1:
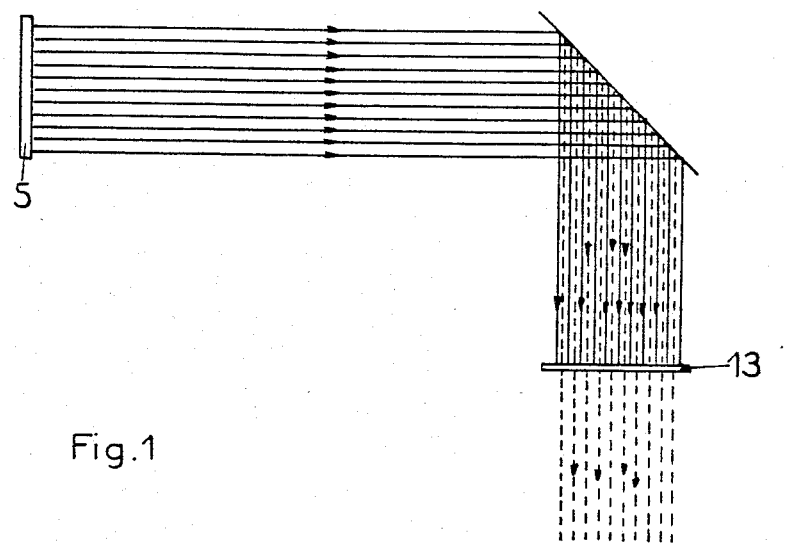
FIG. 1 is a diagram showing a light path from source to image according to the present invention.

As illustrated schematically in FIG. 1, the process according to the invention for forming an image of the eye for photographing and/or observation, the image being free from reflections off the eye or the prosthesis due to a light source emitting rays selected, e.g., to excite a fluorescent substance dropped into the eye, includes selecting only those rays appropriate for the fluorescent substance, i.e., only those rays which will excite the substance and not reflect off the eye or the prosthesis. Accordingly, the light source wavelengths, represented by solid lines in FIG. 1, are less than or equal to a value $\lambda 1$ adapted for exciting the fluorescent substance in the eye and corresponding to the smallest wavelength of radiation emitted by the fluorescent substance.

The rays emitted by the fluorescent substance are represented by the dotted lines in FIG. 1. The process of the invention avoids interference between the two radiations, or the two ranges of rays, emitted by the source of light and by the fluorescent substance, respectively, thus eliminating all reflections. In performing tests, preferably a fluorescent substance, fluorocein, which emits radiation having a wavelength λ1 which is appreciably equal to or greater than 500 nm.

The range of rays issuing from the eye include rays emitted by the fluorescent substance and luminous rays reflected and/or diffused off the eye and/or the ocular prosthesis. To eliminate reflections from the light source which may mask zones in the image whose observation is necessary for a correct analysis of the test results, the rays issuing from the eye are filtered to select only rays with a wavelength greater than λ1 such that only such wavelengths are allowed to pass through the filter. Accordingly, only those rays appropriate for or characteristic of the fluorescent substance are selected. Luminous rays from the light source, reflected off the eye and the prosthesis having wavelength less than λ1 are therefore eliminated by the filter.

Moreover, the present invention also provides apparatus which has an object to improve the contrast between zones of the eye which are provided with fluorescent substance, and are therefore glowing, and zones which are free from fluorescent substance, and are therefore dark, providing for complete extinction of that portion of the light from the light source which would tend to be reflected off the eye and/or the prosthesis.

Figure 2:
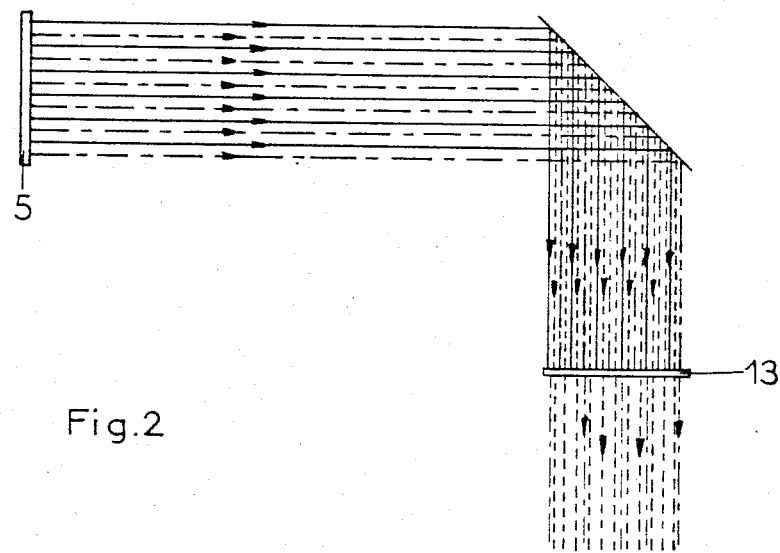
FIG. 2 is a diagram of the light path when white light is also emitted from the source.

When analyzing an image of an eye, it is sometimes necessary to illuminate zones not provided with fluorescent substance, without, in so doing, reducing the contrast and preferably, without introducing reflections into the image. To this end, a variation of the process according to the invention, illustrated in FIG. 2, includes adding a beam of white light to the radiation emitted by the light source. The beam of white light is represented by thin mixed lines in FIG. 2. The white light in very small quantities increases the luminosity of the fluorescent substance by furnishing luminous rays of wavelengths greater than λ1 and also illuminating zones of the eye that are not provided with luminous substance, such as the eyelashes and scleral regions, without diminishing the contrast between the two zones, i.e., with fluorescent substance and without f uroescent substance. As is apparent, providing a beam of white light enables the colored shades of the eye to be revealed. Therefore, the scleral vessels, for example, will appear substantially their natural color on the image formed of the eye for photographing and/or observation. Moreover, providing while light enables the detail of the zones provided with fluorescent substance to be revealed.

To remove reflections of the beam of white light off the eye and the prosthesis which are visible in the image to be photographed and/or observed, the white light is polarized before and after its reflection along two correctly oriented planes. Experience shows that these two planes must be perpendicular to each other for their use as described in the present application. The second polarization, i.e., the one after reflection, can be effected before or after filtering of the luminous rays issuing from the eye. It should be noted that elimination of the reflections of the beam of white light at the level of the image of the eye in no way harms its diffusion.

As shown schematically in FIG. 3, apparatus 1 for the practice of the process according to the present invention comprises at least one luminous source 2, for emission of ultraviolet and visible rays of wavelengths less than 1, and one optical instrument 3 for forming an image of the eye for photographing and/or observation, which is associated with a photographic apparatus and/or an observation apparatus. The light source directed toward the eye includes a mounting 4, in which is mounted at least one means for emitting white light, at least one element 5 for selection of luminous rays of wavelengths less than λ1, at least one focusing system, and at least one stopping element 6 for blocking heat waves emitted by means 7.

As shown in FIG. 3, luminous source 2 includes two means, 7 and 8, for emitting white light. Means 7 and 8 comprise, respectively, a halogen lamp and a flash lamp powered by electricity at the time of photographing in a known manner, e.g., by the mechanism of a casing of a camera. Lamp 7 is supplied with a low voltage current by a network of conductors and is intended principally for illuminating the eye at the time of its observation but preferably remains charged at the time of photographing for reasons of simplification of the mounting. It should be noted that for taking a series of pictures, only lamp 7 will be charged. Lamp 7 and flashlamp 8 are connected to each other, each with a mirror directing a major portion of the rays emitted toward selection element 5 which selects rays of wavelengths less than λ1. Lamp 7 and associated parabolic mirror 9 are mounted at the end of mounting 4, preferably outside of the latter to facilitate thermal exchange with the exterior environment.

Preferably, flash lamp 8 is of the type having the shape of a tubular cylindrical element in a U-shape and is arranged with its mirror 10 on the interior of mounting 4 such that the plane of the U is perpendicular to the longitudinal axis of source 2, with the branches of the U arranged on both sides of that axis for reasons which will be explained below. Luminous rays issuing from lamp 7 and/or flash lamp 8 are filtered by element 5, which is shown formed as a screen for rays of wavelengths greater than λ1.

Element 5, which is a filter, is arranged in the path of the luminous rays and is preferably mounted at the end of mounting 4, facing the eye to be examined.

According to a preferred embodiment, element 5 is a filter which allows only visible and invisible rays of wavelengths of less than 500 nm to pass therethrough. To avoid shadows on the zone to be photographed, for example, due to the interception of luminous rays issuing from lamp 7 by flash lamp 8, and to concentrate the entirety of the rays of wavelengths of less than λ1 on said zone, source 2 is provided with an optical focusing system.

According to the embodiment shown in FIG. 3, the optical focusing system has a first arrangement 11 of lenses situated in the path of the luminous rays of lamp 7 and a second arrangement 12 of lenses disposed in the path of the bright rays issuing from source 2. Lens arrangement 11 associated with mirror 9 of lamp 7 is provided to focus luminous rays issuing from lamp 7 and/or reflected on mirror 9 on a point situated on the axis of source 2, preferably between the branches of flash lamp 8. It should be noted that the position of the focal point on the axis is only given by way of example, the object thereof being to space the conical envelope of rays issuing from lamp 7 from the flashlamp. Lens arrangement 12, situated in the path of luminous rays issuing from source 2, avoids dispersion of these rays by concentrating them on the zone of the eye to be photographed and/or observed.

Preferably, lens arrangement 12 focuses the rays issuing from source 2 behind the observed zone, but can, according to a variation of this embodiment, focus them in front thereof.

According to another embodiment of the invention, the arrangement of lenses 12 can be replaced by an optical system which will allow for the variation of the focal point of the rays leaving the eye for illumination of the zones of observation to different extents. Source 2 is provided with an element for stopping heat rays emitted by lamp 7, the element being composed of a catathermic filter 6 arranged in the mounting between the arrangement of lenses 11 and flash lamp 8 or between lamp 7 and arrangement of lenses 11. To aid in the elimination of heat waves, mirror 9 is of a dichroic type, allowing for the refraction of heat rays.

As previously stated, rays of wavelengths less than $\lambda 1$ excite the fluorescent substance dropped into the tears of an eye; the fluorescent substance emits one or a spectrum of luminous rays of wavelengths greater than $\lambda 1$. To select rays appropriate for the fluorescent substance and to remove light from the source which is reflected off the eye and/or the prosthesis, optical instrument 3 of apparatus 1 is equipped with a filter 13 for selecting rays of wavelengths greater than $\lambda 1$, i.e., permitting rays of wavelengths greater than $\lambda 1$ to pass therethrough. Instrument 3 is directed toward the eye to be photographed and/or observed and includes a mounting 14, in which are arranged one or several lens arrangements 15 for forming the image of the eye. Connected to mounting 14 are a camera casing and/or an observation apparatus known in the art and preferably mounted on slides for arrangement facing orifice 14A of the mounting. Filter 13 is arranged in the mounting behind lens arrangement or arrangements 15 and in the path of the luminous rays leaving the eye, and is connected to the mounting by any suitable means.

According to another embodiment of the invention, the apparatus is equipped with at least one means of emission of a beam of white light, concurrently with the emission of rays of wavelength less than $\lambda 1$, for illuminating zones of the eye free from the fluorescent substance and for increasing the luminousity of the fluorescent substance. Preferably, the means for emission of the beam of white light comprises lamp 7 and/or flashlamp 8. To this end, as shown in FIG. 5, filter 5, which selects rays of wavelengths less than $\lambda 1$, is provided with at least one transverse orifice 16, of small dimension, which allows only a very low quantity of white light to pass filter 5.

To remove visible reflections from the image in the zone to be photographed and/or observed, arising from reflection of the beam of light off the eye and/or the prosthesis, the white light is polarized before and after its reflection by filters 17 and 18 located respectively in source 2 and optical apparatus 3. As shown in FIG. 4, filter 17 is of slightly greater dimension than the diameter of orifice 16 and is attached on one surface of filter 5 facing the orifice. Filter 18 of optical apparatus 3 is preferably disposed in the mounting after the arrangement of lenses 15. The polarization plane of filter 18 is perpendicular to that of filter 17 to remove from the formed image of the eye reflections caused by the beam of white light.

Figure 6:
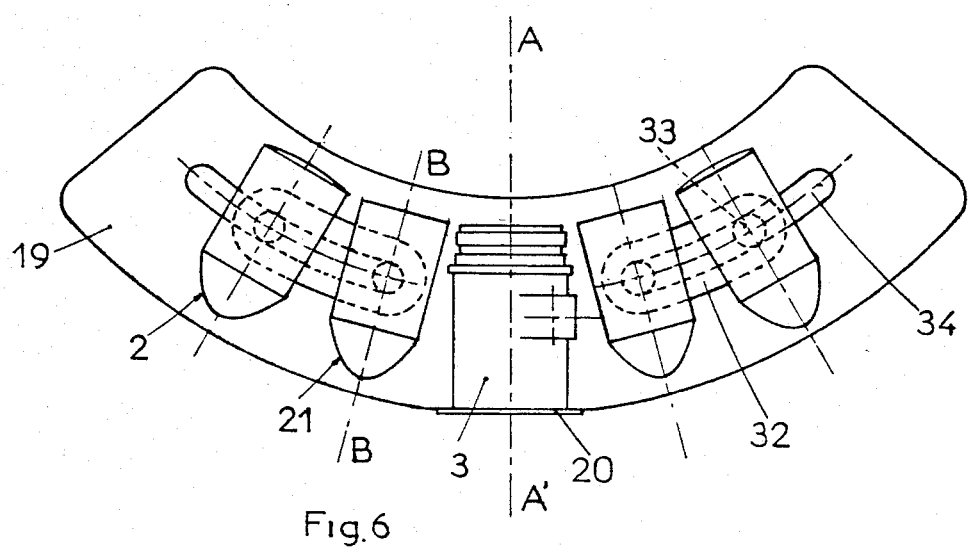
FIG. 6 is a planar view of another embodiment of the present invention.

Preferably, the zone of the eye to be examined is illuminated from several angles to assure an equal distribution of light. To this end, according to a preferred embodiment of the invention, apparatus 1 is equipped with two light sources 2 fed by the same electrical circuit and is arranged on both sides of the axis A—A', equidistant from the eye to be examined, as shown in FIG. 6. As seen in FIG. 6, luminous sources 2 and optical apparatus 3 are mounted on a horizontal plate 19 conforming, for reasons of bulk, to the shape of a sector of a corona. Plate 19 is provided with an upwardly directed vertical wing 20 to which is fixed mounting 14 of apparatus 3 by any suitable means and the slides not represented of the photographic and/or observation apparatus. To allow taking a picture of, or observing, the eye in white light, apparatus 1 is equipped with at least one source 21 for emission of white light and with means for retracting filter 13 from the path of luminous rays issuing from the eye.

Preferably, for reasons previously stated, apparatus 1 is equipped with two sources 21 of white light fed by the same electrical circuit arranged on both sides of axis A—A' of apparatus 3 and between apparatus 3 and sources 2, as shown in FIG. 6.

Figure 7:
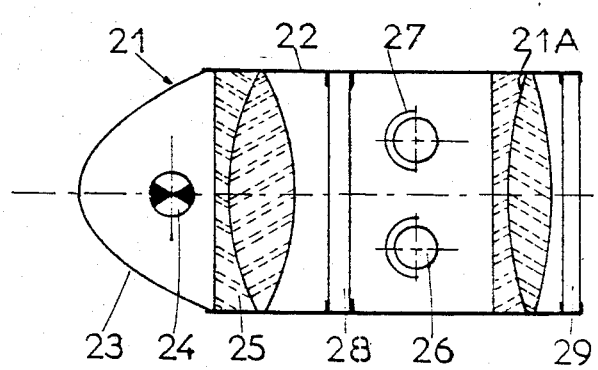
FIG. 7 is a schematic view of a soource of white light.
Figure 8:
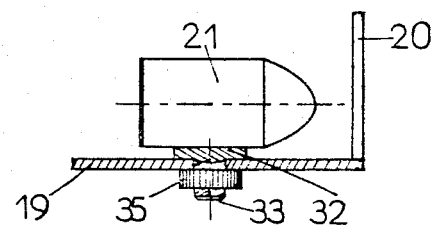
FIG. 8 is a cut-away view along line B—B of FIG. 6.

As shown in FIG. 7, each source of white light includes a mounting 22, a parabolic mirror 23 connected to a halogen lamp 24, a set of lenses 25 for focusing the rays emitted by the lamp 24 between the arms of flashlamp 26 connected to mirror 27, a catathermic filter 28, and a diffuser 29, for providing a uniform distribution of light on the eye to be examined. The operation of the two diffusers 29 and the illumination from two different angles allows for the suppression of shadows due, for example, to eyelids, eyelashes, etc. Furthermore, the diffuser does not alter the characteristic of the white light emitted, and allows colored shades of the eye to be distinguished and anomalies to be detected. Preferably, each source 21 is equipped with a set of lenses 21 disposed before or after the diffuser for concentrating the rays leaving the source.

During a test in white light, filter 13 must not intercept the luminous rays leaving the eye. To this end, as shown schematically in FIG. 3, filter 13 is mounted on a mobile shutter 30 in mounting 14 around an axis perpendicular to axis A—A' so the filter may be moved to be arranged parallel to the path of the luminous rays and against the inner wall of mounting 14. Shutter 30 may, for example, comprise a frame on which is fixed the border of filter 13, and which includes an extension from one of its borders a cylindrical shaft 31 journalled in the orifices of mounting 14. One end of shaft 31 extends outside of the mounting 14 and under plate 19 and cooperates with a grooved button (not shown) to control the mobile shutter.

In operation, the sources of white light cause reflections off the eye and/or the ocular prosthesis which are visible in the image of the eye formed for observation. This condition is not troublesome to the extent that the reflections are situated outside of the zones of the eye to be examined. As a function of the zone of the eye chosen for the test, the sources of white light 21 are capable of being spaced or brought together while still remaining equidistant from the eye.

To assure that the position of the reflections does not vary at the time of photographing, lamp 24 is coaxial with the axis of symmetry of source 21, and the arms of the flash lamp are arranged symmetrically on both sides of this axis. Preferably, this characteristic is reproduced with respect to sources 2 to allow for the localization of reflection of the beam of white light when such light is not polarized.

According to the preferred embodiment shown in FIG. 6, the sources of light 21 are each mounted on a mobile support 32, which follows an arc of a circle with respect to plate 19. This support 32 for example a metal plate provided with two guiding pieces 33 engaged in groove 34 which is in the form of a circular arc in plate 19 centered with respect to the eye such that in the course of angular movement tending to either separate or bring together the sources, the sources are always directed toward the same point on axis A—A'. One of the guiding pieces of each support is threaded to receive a grooved button 35 for locking source 21 into position with respect to plate 13. Preferably, sources 2 for the emission of wavelengths less than λ1 are each attached to a support 32 to increase the spacing of sources 21 and to localize reflections in the manner previously stated.

The reflections off the eye and/or the ocular prosthesis of the white light from sources 21 can be attenuated, as known, by polarizing filters arranged, respectively, in the path of luminous rays leaving the sources and in the path of light rays penetrating the optical apparatus 3. Preferably, filter 18 of the embodiment of FIGS. 4 and 5 can be used as well in the polarization of luminous rays leaving the eye when the eye is illuminated with white light.

According to a variation of this embodiment, the polarizing filters are each mounted on a mobile shutter in front of sources 21 and apparatus 3 to intercept or not the path of the light rays. Light sources 2 and 21 are mounted in series, respectively, on two independent circuits successively charged by a two-position switch. Preferably, this switch comprises two pushbuttons controlled one after the other by a cam mounted on shaft 31 behind mounting 15. When filter 13 of optical apparatus 3 is perpendicular to axis A—A', the cam acts only on the pushbutton to charge the electrical control circuit for controlling light sources 2. Conversely, when filter 13 is parallel to axis A—A', the cam acts only on the pushbutton to charge only the electrical control circuit of white light sources 21. Each control circuit includes a low-voltage feed for lamps 7 or 24 and an electrical system synchronized with the shutter of the photographic apparatus case for the ignition of flash lamps 8 or 26.

Apparatus 1 may be protected by a shell, e.g., formed of polyester, attached to plate 19 by any suitable means. At least one of the inner walls of the shell is preferably bored to provide orifices for the release of heat from sources 2 and 21.

Figure 9:
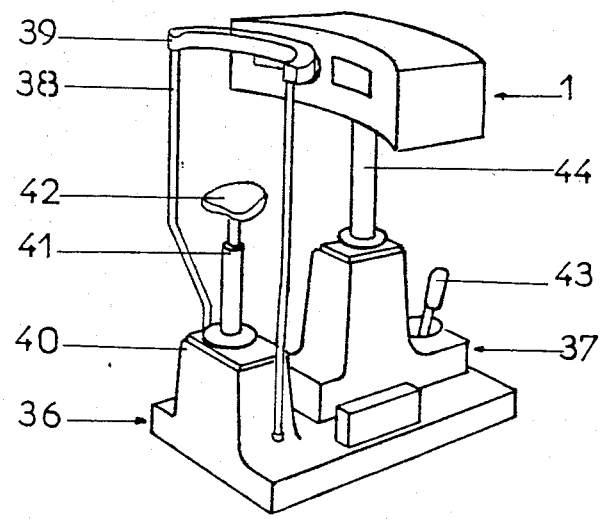
FIG. 9 is a perspective view of an apparatus according to the present invention.

As shown in FIG. 9, apparatus 1, as noted above, is associated with means for positioning apparatus 3 and sources 2 and 21 opposite the eye to be examined. These means comprise a frame 36 resting on a working plane and a mobile cart 37 carrying apparatus 1. Frame 36 may be rectangular and is provided with an armature with four elastic support elements for the working plane covered with a dressing preferably including a polyester shell. Two substantially vertical posts 38 are attached to frame 36 and carry at their upper end a tapered head support 39 arranged in a horizontal plane.

Between posts 38, attached to portion 40 of frame 36, is a vertical telescopic shaft carrying on one end a chin rest 42. In case 1 there are mounted different electrical power feed elements for luminous source 2 and/or sources of white light 21. At least one of the inner walls of case 1 is pierced with orifices for releasing heat from the electrical elements.

Behind case 40, the frame is provided with means for guiding mobile cart 37 along two perpendicular directions of a horizontal plane to dispose apparatus 1 such that it faces the eye to be examined and to adjust the distance to the eye. The guidance means acts in conjunction with a handle 43 of the cart, mounted on a swivel joint. Mobile cart 37 is provided with a vertical column 44, preferably telescopic and integral with plate 19 of apparatus 1.

Figure 10:
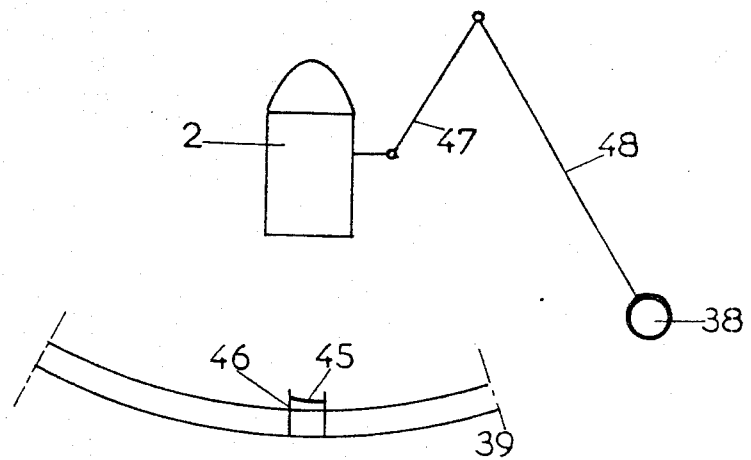
FIG. 10 is a view showing a backlighting system according to the present invention.

The apparatus according to the invention is particularly adapted for photographing and/or observing an eye equipped with an ocular prosthesis, but can be employed for photographing and/or observing an ocular prosthesis which is back-lit by a light source 2 or by a source of white light 21. To this end, as represented schematically in FIG. 10, occular prosthesis 45 is supported by a removable support 46 attached to support head 39 such that it faces optical apparatus 3. Lighting source 2 or 21 is mounted at the end of lever assembly 47 and 48 such that it can be positioned along the extension of axis A—A' of apparatus 3 and behind prosthesis 45. Lever 47 is joined at one of its ends to source 2 or 21 and at the other end to lever 48. Lever 48 is joined to one of the posts 38 of frame 36.

Apparatus 1 according to the invention for photographing and/or observing an image of an eye is particularly useful in the fitting of ocular prostheses, but can be associated also with means for thorough classic opthamologic tests, such as slit lamps and others.

It is believed that the advantages and improved results furnished by the method and apparatus of the present invention are apparent from the foregoing description of the preferred embodiments of the invention. Various changes and modifications may be made without departing from the claims which follow.

I claim:

1. A method of forming an image of an eye, comprising the steps of:
   (a) partially coating the eye with a fluorescent substance;
   (b) exposing the eye coated with fluorescent substance to radiation from a radiation source so as to excite the fluorescent substance to emit radiation, said radiation from said radiation source being reflected on the eye, the wavelengths of the radiation from the radiation source and reflected off the eye being less than or equal to the smallest wavelength of the radiation emitted by the fluorescent substance; and
   (c) filtering radiation emitted by the fluorescent substance and radiation from the radiation source and reflected off the eye to select radiation emitted by the fluorescent substance, so as to increase the contrast between the portion of the eye coated with the fluorescent substance and the portion of the eye not coated with the fluorescent substance.

2. The method of claim 1 wherein said radiation emitted by said fluorescent substance is filtered at a point between the eye and the image of the eye.

3. The method of claim 2 wherein said fluorescent material is excited to emit radiation when exposed to radiation in the range of said smallest radiation wavelength.

4. The method of claim 3 wherein radiation having a wavelength less than said smallest radiation wavelength emitted by said fluorescent substance when excited by said radiation source is filtered between the eye and the image of the eye.

5. The method of claim 1 wherein the eye is also exposed to white light.

6. The method of claim 5 wherein the white light is reflected off the eye, said white light being polarized before and after said white light is reflected off the eye, the two polarizations being along planes perpendicular to each other.

7. The method of claim 1 wherein the minimum wavelength of the emitted radiation of the fluorescent substance is 500 nm.

8. An apparatus for forming an image of an eye, said eye being at least partially coated with a fluorescent substance, comprising:
   (a) a first means for exposing an eye to radiation having wavelengths all of which are less than or equal to the smallest radiation wavelength emitted by said fluorescent substance when excited by said radiation from said means for exposing an eye to radiation; and
   (b) a first filter for selecting radiation emitted by said fluorescent substance located in the optical path of radiation emitted by said fluorescent substance.

9. The apparatus of claim 8 wherein said first filter is disposed between the eye and the image of the eye.

10. The apparatus of claim 9 wherein said first filter eliminates radiation having a wavelength less than said smallest radiation wavelength emitted by said fluorescent substance.

11. The apparatus according to claim 10 wherein said first source of radiation comprises a first lamp which generates radiation of wavelengths less than or equal to the smallest wavelengths emitted by said fluorescent substance when excited by said radiation and white light wavelengths, said apparatus further comprising:
   (a) a second filter in communication with said first lamp and disposed between said first lamp and the eye for allowing all radiation having wavelengths less than or equal to the smallest wavelength emitted by said fluorescent substance when excited by said radiation to pass but allowing only a small quantity of white light wavelengths to pass, and
   (b) means for polarizing white light wavelengths before and after said white light wavelengths are reflected off the eye in association with said second filter.

12. The apparatus of claim 1 wherein said means for polarizing white light comprises elements for polarizing light along names perpendicular to each other.

13. The apparatus of claim 12 further comprising:
   (a) a second source of radiation for emission of white light wavelengths, said second source of radiation being independently operable with respect to said first source of radiation, said first source of radiation and said second source of radiation being positioned adjacent each other; and
   (b) means for removing said first filter from between the eye and the image such that the eye can be observed solely in white light, said means for removing being mounted in the front of said second source of radiation.

14. The apparatus according to claim 11 wherein said second filter comprises at least one transverse orifice for passing a small quantity of white light.

15. The apparatus according to claim 13 wherein said first and second source of radiation each comprise a pair of light sources, each light source being adjustably positioned on an arc and disposed symmetrically with respect to a first axis which is formed by a line substantially through the eye and the location of the image of the eye to be observed.

16. The apparatus of claim 1 wherein said first source of radiation further comprises a flash lamp.

17. The apparatus of claim 16 wherein said flash lamp is of a type having a tubular cylindrical element in the shape of a U, the plane of said U-shape being perpendicular to a second axis which is formed by a line substantially through said first lamp and the eye to be observed, said flash lamp having branches arranged on both sides of said second axis.

18. The apparatus of claim 17 wherein said first source of radiation further comprises:
   (a) a mirror positioned posterior to said first lamp to reflect the radiation from said first lamp toward the eye, and
   (b) first lens disposed anterior to said first lamp and said mirror for focusing radiation directly emitted from said first lamp and radiation from said first lamp which is reflected from said mirror.

19. The apparatus of claim 18 wherein said first lens means is adapted to focus radiation emitted directly from said first lamp and radiation from said first lamp which is reflected from said mirror onto said second axis at a point between said branches of said flash lamp.

20. The apparatus of claim 17 wherein said flash lamp is in communication with a camera, thereby permitting said flash lamp to be triggered by said camera.

21. The apparatus of claim 18 further comprising second lens arranged anterior to said first lens for focusing radiation emitted by said fluorescent substance.

* * * * *